United States Patent [19]

Paustian et al.

[11] 3,944,598

[45] Mar. 16, 1976

[54] PRODUCTION OF AMINE SALTS OF CARBOXYLIC ACIDS

[75] Inventors: John E. Paustian, Whippany; Abraham P. Gelbein, Plainfield, both of N.J.

[73] Assignee: The Lummus Company, Bloomfield, N.J.

[22] Filed: June 21, 1973

[21] Appl. No.: 372,047

[52] U.S. Cl. ........ 260/501.1; 260/248.5; 260/295 S; 260/295.5 S; 260/347.3; 260/501.16; 260/501.2

[51] Int. Cl.$^2$ .................. C07C 87/00; C07D 295/00; C07D 213/00; C07D 307/00

[58] Field of Search .......... 260/515 P, 501.1, 501.2, 260/576, 248.5, 295 S, 295.5 S, 347.3, 501.16

[56] References Cited
UNITED STATES PATENTS 3,113,964   12/1963   Farkas et al. .................... 260/515 P 3,776,949   12/1973   Gelbein et al. ................. 260/515 P

OTHER PUBLICATIONS

Roberts et al., "Basic Principles of Organic Chemistry," pp. 554–555 (1965).
March "Advanced Organic Chemistry," p. 660 (1968).

*Primary Examiner*—James O. Thomas, Jr.
*Assistant Examiner*—Nicky Chan
*Attorney, Agent, or Firm*—Marn & Jangarathis

[57] ABSTRACT

Amine salts of aromatic and aliphatic carboxylic acids are produced by hydrolysis of a corresponding nitrile, imide, amide or mixtures thereof in the presence of an amine, and stripping of evolved ammonia. The amine salts may be used in separation of certain isomeric acids, and are useful as intermediates in the production of the corresponding carboxylic acids and derivatives thereof, such as esters and anhydrides.

17 Claims, No Drawings

PRODUCTION OF AMINE SALTS OF CARBOXYLIC ACIDS

BACKGROUND OF THE INVENTION

The present invention relates to the production of amine salts of aromatic and aliphatic mono- and polycarboxylic acids. Such salts, as disclosed in our copending application Ser. No. 436,861, filed Jan. 28, 1974, have utility as intermediates in the preparation of the corresponding carboxylic acids and derivatives thereof, such as esters and anhydrides. Amine salts may also be useful in the separation of isomeric carboxylic acids. U.S. Pat. No. 2,664,440, for example, discloses the separation of isophthalic and terephthalic acids by conversion of the acids to the amine salts, which are more readily separated, by fractional crystallization, followed by reconversion to the acid.

Amine salts of carboxylic acids are usually produced by reacting the acid with an amine, often in aqueous solution. The usual commercial method of producing aromatic carboxylic acids and their anhydrides is by air oxidation of a corresponding lower alkyl (e.g. methyl-, ethyl- or propyl-) benzene, in the presence of a catalyst. Aliphatic carboxylic acids, both saturated and unsaturated, can also be made by air oxidation, in the presence of a catalyst, from the corresponding paraffin or olefin containing a terminal methyl group. Such processes generally result in the production of undesirable by-products, e.g., other carboxylic acids and aldehydes, in addition to the desired acid or anhydride. Generally, such by-products must be removed for the acid to be commercially useful.

Another method of producing carboxylic acids is by conversion of the corresponding hydrocarbons to nitriles, followed by conversion of the nitriles to acids, e.g. by hydrolysis. Aromatic carboxylic acids have been produced by both catalytic and non-catalytic hydrolysis of a corresponding nitrile, with stripping of ammonia from the hydrolysis product, and by hydrolysis to ammonium salts and thermal decomposition of the salts to the free acid. In such processes, however, large amounts of steam or other stripping gas and other utilities may be required. Additionally, subsequent purification of the acid may be required to eliminate nitrogenous by-products, such as intermediate products of the nitrile hydrolysis.

It has also been known to similarly produce various carboxylic acids, or ammonium salts thereof, by hydrolysis of the corresponding amides or imides.

It is an object of this invention to provide a new, improved process for hydrolysis of aromatic and aliphatic nitriles.

A second object of the present invention is to produce amine salts of aromatic and aliphatic mono- and polycarboxylic acids without requiring the production of the acid as an intermediate compound. Another object of the present invention is to provide amine salts for use as intermediates in the production of carboxylic acids and derivatives thereof. A third object of this invention is to produce amine salts of carboxylic acids from corresponding nitriles, amides, imides or mixtures thereof. Yet another object of this invention is to prepare amine salts of carboxylic acids from corresponding hydrocarbons. Still another objective of this invention is to provide amine salt intermediates for the production of carboxylic acids from corresponding hydrocarbons without also producing undesirable oxidation by-products.

SUMMARY OF THE INVENTION

In one aspect, the invention described herein comprises the aqueous hydrolysis of nitriles, imides, amides and/or mixtures thereof in the presence of an amine, with removal of evolved ammonia, preferably by stripping, to produce the amine salt or salts of the corresponding carboxylic acids.

In another aspect, the invention comprises the production of amine salts of carboxylic acids from corresponding hydrocarbons by first contacting such hydrocarbon with ammonia, either in the presence of free oxygen and a catalyst or in the presence of a catalyst which can supply oxygen to the reaction to form the corresponding nitrile or mixture of nitrile and imide followed by hydrolyzing the nitrile or nitrile-imide mixture in the presence of an amine, as above.

DETAILED DESCRIPTION AND PREFERRED EMBODIMENTS

For convenience, the nature of the invention will be primarily illustrated in the following text by the production of amine salts of phthalic acid from the products of the reaction between ortho-xylene, ammonia and oxygen, by hydrolysis in the presence of trimethylamine. However, as discussed in detail hereinbelow, the process is applicable to a wide variety of carboxylic acids and amines.

Processes for preparing mono- and polynitriles by catalytic reaction of corresponding hydrocarbons with ammonia and oxygen are well known in the art. Generally speaking, such processes involve the use of free oxygen (usually as air), in which case the process is usually referred to as ammoxidation. Alternatively, as disclosed in U.S. application 147,159, filed May 26, 1971, copending herewith, and assigned to the assignee hereof, the process can also be carried out in the absence of free oxygen, in the presence of a catalyst which contains oxygen combined therein, and which is utilized to both catalyze the reaction and supply the oxygen, the catalyst being partially reduced in the process. Such a process may be referred to as ammonolysis.

Such reaction (in the case of methyl-substituted benzenes) produces primarily the nitrile corresponding to the methylbenzene, or in the case of polymethylbenzenes, a mixture of the desired polynitrile and other nitriles. In the case of methylbenzenes having one or more pairs of methyl groups in the ortho position with respect to each other, the reaction products will contain some amount of the corresponding cyclic imide (e.g. phthalimide.)

The reaction, in general, for compounds which do not have two methyl groups in the ortho position on the aromatic ring can be represented as:

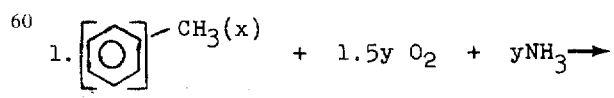

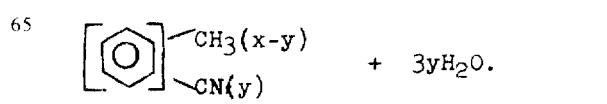

In the case of aromatic compounds having one or more pairs of methyl groups in the ortho position on the aromatic ring, however, additional reactions are also possible. In the case of ortho-xylene, for instance, the following reactions may occur:

tion from the desired nitrile.

Other nitriles, such as o-tolunitrile, will also be hydrolyzed to amine salts of their corresponding carboxylic acids. Separation of these nitriles or the amine salts or other carboxylic acid derivatives, from the desired

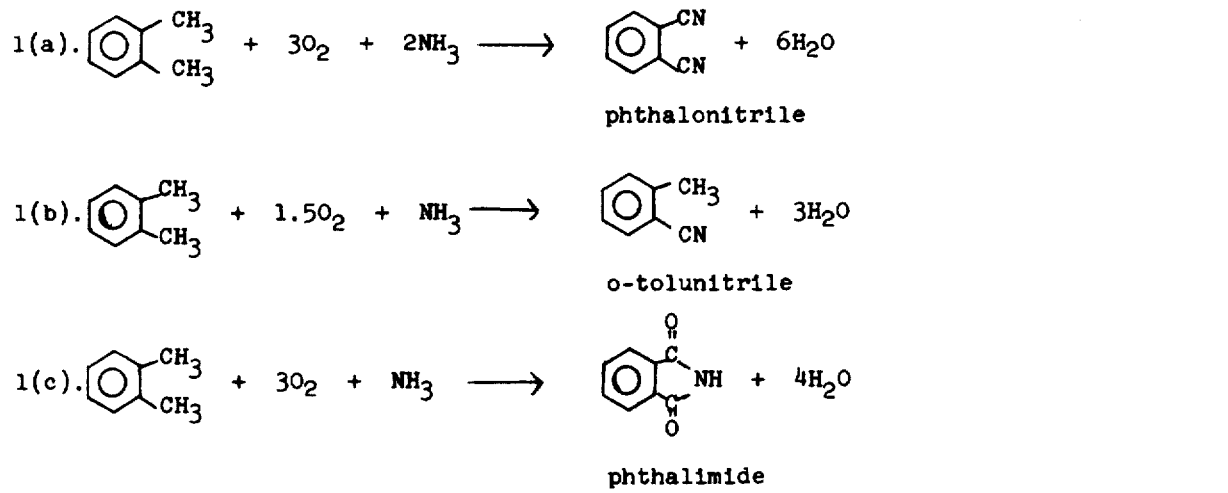

phthalonitrile o-tolunitrile phthalimide

Generally, in the reaction of ortho-xylene to produce phthalonitrile, all three reactions will occur to some extent, and the product will contain some o-tolunitrile and phthalimide.

In commercial practice today, phthalimide is regarded as an undesirable by-product or contaminant and steps are taken to prevent its formation or separate it from the desired nitrile. As will be pointed out below, however, the presence of phthalimide will not be detrimental in the utilization of the present invention, as it will be converted to the desired amine salt. Phthalimide may in fact be considered desirable in that it is hydrolyzed even more readily than the nitrile.

Analogously, the reaction of other aromatic compounds having ortho-dimethyl (or other lower-alkyl) configurations, such as durene, pseudocumene and ortho-dimethylnaphthalenes, with ammonia and oxygen will result in the production of some imide, which can be converted to the desired amine salt by the process of our invention without necessitating its separation from the desired nitrile.

product, may be necessary to avoid contamination of the final product.

The ammoxidation or ammonolysis reactions are generally conducted at temperatures of 600° to 1000° F, total pressures of 1 to 5 atmospheres, residence times of 1 to 30 seconds and feed compositions containing from stoichiometric amounts of reactants to large excesses of $O_2$ and $NH_3$ with or without diluents.

The products of the ammoxidation or ammonolysis reaction are, according to the invention, then subjected to an aqueous hydrolysis step under pressure and at elevated temperatures, in the presence of an amine, which may be either a primary, secondary, or tertiary amine, with continous removal of ammonia evolved, to convert the reaction products to the amine salt of the corresponding mono-or polycarboxylic acid and ammonia.

The hydrolysis of the phthalonitrile-phthalimide mixture with trimethylamine proceeds according to the following reactions, depending on the feed:

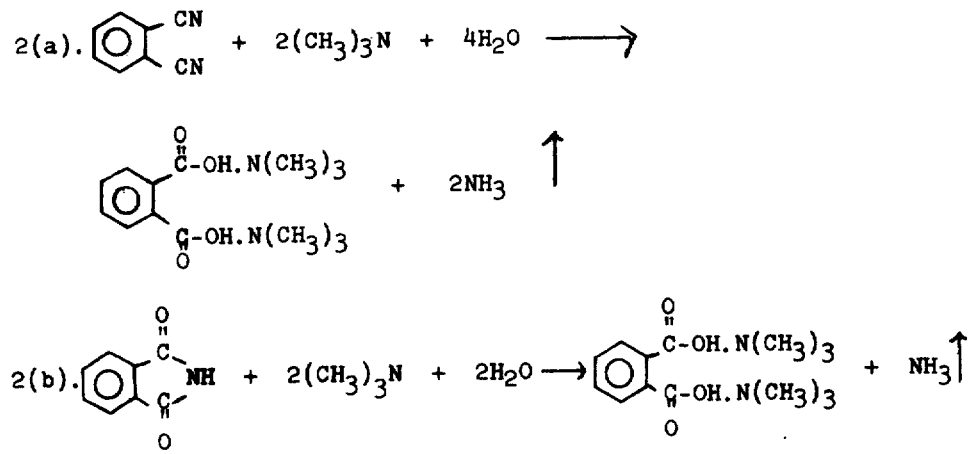

The hydrolysis is carried out at temperatures of between 150° and 500° F, preferably between 200° and 450° F, under autogenous pressure of the system. The ammonia evolved is removed from the reaction products, preferably by countercurrent stripping with steam or other suitable inert gas (e.g. helium, methane, paraffins, etc.).

In one preferred embodiment, the hydrolysis is carried out in a continuous fashion, preferably in a vertically disposed reactor, with continuous introduction of reactants and withdrawal of products. Alternatively, the hydrolysis could be conducted as a batch process. In the first case, ammonia is preferably stripped by introducing the stripping gas into the hydrolysis reactor countercurrently to the flow of reactants, so that all operations can be carried out in one reactor. If a volatile amine is utilized, some will be stripped along with the ammonia and provision should be made for separation and recycling or refluxing the amine to the reactor. As mentioned subsequently, hydrolysis of certain nitriles may require stripping of ammonia as it is formed; this method permits such stripping. Alternatively, for most nitriles, the reaction products can be continuously stripped in a second piece of apparatus. In a batch operation, stripping will generally be performed in a subsequent step, either in the same or another piece of apparatus.

As the hydrolysis reaction (reactions 2a or 2b) will be carried out in excess water and the amine salts are water-soluble, the products will remain in solution and the mixture will contain, for example, phthalate, hydroxyl, ammonium, and trimethylammonium ions, as depicted in the following reactions 3–5:

$$(CH_3)_3N + H_2O \rightleftarrows (CH_3)_3NHOH \rightleftarrows [(CH_3)_3NH]^+ + [OH]^- \tag{3}$$

$$NH_3 + H_2O \rightleftarrows NH_4OH \rightleftarrows [NH_4]^+ + [OH]^- \tag{4}$$

$$(CH_3)_3N + [NH_4]^+ \rightleftarrows [(CH_3)_3NH]^+ + NH_3 \tag{5}$$

Analogous reactions take place for salts of other amines and other acids as this class of compounds is generally watersoluble, and the products of the reaction will, in general, be an aqueous solution containing carboxyl anions and alkyl substituted ammonium cations.

Since aliphatic amines are more basic than ammonia (for example the dissociation constant of ammonia is 4.75, that of trimethylamine is 4.20, and that of triethylamine 3.36) the equilibrium of reaction 5 will be shifted to the right and that of reaction 3 will be more to the right than that of reaction 4. The higher concentration of hydroxyl ions will therefore effect hydrolysis of the ammoxidation or ammonolysis reaction products more rapidly than will ammonium hydroxide (i.e., ammonia) alone. In addition, separation of ammonia for recycle to the ammoxidation or ammonolysis reactor is facilitated (reaction 5).

One advantage of the present invention is that carboxylic acids and derivatives thereof may be produced from the reaction products of the amine hydrolysis-ammonia stripping step without actual recovery of the amine salts from the aqueous solution. However, it may be in some cases advantageous to recover these salts, as for example in the case in which the process is being performed to effect the separation of terephthalic and isophthalic acids, e.g., as disclosed in U.S. Pat. No. 2,664,440, in which case the salts will be separated and recovered by fractional crystallization. Additionally, the solution can be treated by evaporation or other conventional methods to recover the amine salts as solids, in the event that these salts are to be stored or shipped for further treatment in another location or at a subsequent time.

The amine utilized in this reaction cay be any amine which is preferably at least as basic as ammonia and has sufficient solubility in water under the processing conditions employed to ensure adequate hydroxyl ion concentration. In selecting the amine, consideration should be given to the possibilities of complications (e.g. side reactions or reactions between two amine molecules) which may occur in some situations when amines are having additional functional groups are utilized. For example, depending on operating conditions, amines having functional groups such as ethers, halogen atoms, nitro groups of unsaturation, may undergo, respectively, cleavage, hydrolysis, thermal decomposition or polymerization or addition reactions. Use of a hydroxylamine may involve the possibility of an esterification reaction with the nitrile. On the other and, alkanolamines having relatively low volatility and adequate water solubility may be useful because of these properties, for example, in the hydrolysis of cyanohydrins.

The amines utilized may be primary, secondary or tertiary. Aliphatic amines, including cyclical amines such as hexamethylenetetraamine are preferred, with low molecular weight tertiary aliphatic amines preferred, particularly trimethylamine. Other suitable aliphatic amines are, for example, methylamine, dimethylamine, ethylamine, diethylamine, dimethylethylamine, diethylmethylamine, triethylamine, triethylenediamine, hexamethylenetetraamine, N,N,N', N'-tetramethyl-1,3-butanediamine and quinuclidine. Aromatic amines with an alkyl group between the amine group and aromatic group would also be useful. Typical examples are benzylamine and xylylamine and N-substituted analogues thereof. Pyridine and some of its methylsubstituted derivatives such as picolines and lutidines should also be effective, given sufficient time and temperature, because of their solubility in water, even though they are less basic than ammonia, as ammonia is much more volatile and can be stripped off as it forms.

Treatment of unsaturated aliphatic nitriles, particularly those in which the C—C unsaturation is conjugated with the unsaturated cyano group, requires precautions to prevent addition of ammonia or amines across the carbon-carbon double bond, producing compounds other than those desired. For example, methyacrylonitrile will add ammonia across the double bond to form 2-methyl-2-aminopropionitrile, which will hydrolyze to the amine salt of the corresponding acid rather than that of methyacrylic acid. Thus tertiary amines must be utilized here since primary and secondary amines can also add across the double bond similarly to ammonia while tertiary amines cannot. It is believed that tertiary amines, being more basic than ammonia, may also serve to block ammonia from adding across olefinic bonds, especially when present in large excess. Close regulations of feed:reactant ratios coupled with regulation of stripping to remove ammonia from the reaction mixture as it forms should also be performed to help prevent ammonia addition.

The widest choice of amines is permitted when the amine salt is to be recovered as such; subject to the limitations mentioned above, from the primary, secondary, and tertiary amines suitable for the reaction, the most appropriate amine may be chosen. If the amine salt is to be utilized as an intermediate in the production of other compounds, e.g. acids, anhydrides, esters, or other derivatives of the acids, by processes involving heating (e.g. thermal decomposition of amine salts to the free acid and amine), tertiary amines are preferred. Amine salts of acids with primary or secondary amines may decompose on heating, with the formation of mono-or dialkylamides or N-alkylimides. This is particularly true in the case of amine salts of aromatic acids having carboxyl groups in the ortho position on the ring, e.g. phthalic acid. These will decompose on heating even more readily than other amine salts, forming the corresponding N-alkylimide. Though these can be recycled to the hydrolysis step, as mentioned subsequently, it is preferable to avoid their formation by using tertiary amines.

The process of this invention, in addition to being suitable for producing amine salts of phthalic acid, can be generally used to prepare amine salts of a wide range of carboxylic acids, both aliphatic and aromatic, including heterocyclic, saturated and unsaturated, with and without substituents. These are prepared from corresponding nitriles or, as discussed hereinafter, from corresponding amides or imides.

The process can be used, for example, to prepare amine salts of the following aromatic mono-and polycarboxylic acids from corresponding nitriles, amides, and/or imides: benzoic, phthalic, isophthalic, terephthalic, trimellitic, trimesic, hemimellitic, pyromellitic, prehnitic, mellitic, naphthoic, 1,8-naphthalene-dicarboxylic, 2,6-naphthalene-dicarboxylic and other naphthalene di-and polycarboxylic acids, 2-, 3-and 4-biphenyl carboxylic acids, diphenic acid (2,2'-biphenyl dicarboxylic acid) and other biphenyl di-and polycarboxylic acids, 1-, 2- and 9-anthroic acids, tetrachlorophthalic acid, terephthalamic acid, 4-hydroxyisophthalic acid, phthalaldehydic acid, o-, m- and p-anisic acids, o-, m- and p-hydroxybenzoic acids, vanillic acid, o-, m- and p-toluic acids and other carboxylic acids having substituents on the aromatic ring in addition to the carboxyl group, such as alkyl, alkoxy, hydroxy, halo, amine, etc.

The process may be used as well for the preparation of amine salts of aromatic acids containing one or more heterocyclic atoms in the aromatic ring, for example, nicotinic, isonicotinic, picolinic and furoic acids.

Saturated aliphatic carboxylic acids whose amine salts may be prepared by the process of this invention include, e.g.: acetic, propionic, butyric, isobutyric, valeric, caproic, malonic, succinic, propylmalonic, adipic, glutaric, 2-methylglutaric, mucic, tartaric and citric. Among the unsaturated aliphatic acids whose amine salts may similarly be prepared are acrylic, methacrylic, ethylacrylic, $\beta,\beta$-dimethylacrylic, crotonic, maleic, fumaric, allylmalonic, sorbic, and the various fatty acids. Additionally, amine salts of both saturated and unsaturated aliphatic acids with additional substituents on the carbon chain, e.g., chloroacetic acid may be produced.

Also suitable for use in the process are naphthenic nitriles, producing the amine salts of naphthenic mono- and polycarboxylic acids.

As mentioned previously, imides can also be hydrolyzed to the amine salt of the corresponding carboxylic acids by the present process, either as the sole feed or in a mixture with the nitrile. This becomes particularly important in the production of amine salts of certain acids, for example, phthalic acid, since the present commercial processes for production of phthalonitrile generally also produce phthalimide as well (see equation 1c), sometimes in substantial quantities. Ordinarily the phthalimide must be separated from the nitrile before the nitrile can be further used. In the present invention, however, a mixture of nitrile and imide is quite satisfactory as a hydrolysis feed.

The feed may also include, individually or as a mixture with imides, nitriles or each other, intermediate hydrolysis products of the nitrile such as amides, including mixed cyano-amides (e.g. p-cyanobenzamide), and other similar compounds having a mixture of substituents.

The nature of the invention is further illustrated by the following examples.

EXAMPLE 1

An equimolar mixture of phthalimide and phthalonitrile were charged to an autoclave with a 15 mole % excess of 25% aqueous trimethylamine. The mixture was heated for 4 hours at 150° C with a stirring and ammonia was stripped off. After cooling, the reaction mixture was a clear solution. The total absence of solids indicated a high degree of hydrolysis. Acidification of the solution resulted in the precipitation of a white solid which was identified as phthalic acid by infrared analysis. The homogeneous solution thus contained primarily ammonium and trimethylammonium phthalates.

EXAMPLE 2

Under similar conditions the product of an ammonolysis of ortho-xylene, consisting primarily of phthalonitrile and phthalimide was heated in the presence of water and an excess of triethylamine. Since triethylamine and water are incompletely miscible, the reaction medium consisted of two liquid phases. After 4 hours, at 200° C, and stripping of ammonia, a clear homogeneous solution was obtained, showing the hydrolysis to be essentially complete.

EXAMPLE 3

Preparation of triethylenediamine-benzoic acid salt

Benzonitrile (20.6g, 0.2 mole), triethylenediamine (TEDA) (12.3g, 0.11 moles), and water (77 ml) were charged to a 400 ml stainless steel cylinder fitted with a pressure gauge, pressure relief valve, needle valve, and thermocouple. The benzonitrile was insoluble in water-amine solution and formed a separate layer. The mixture was heated with occasional shaking at 300°F for 24 hours. At this point, the cylinder was vented with the vent gases passed through dilute hydrochloric acid.

An additional 12.3g TEDA and 50 ml $H_2O$ were added and the mixture heated an additional 6 hours at 300°F. After cooling to room temperature, the cylinder was vented through the HCl and the reaction mixture, now a homogeneous solution was transferred to a glass, round-bottomed flask. The mixture was heated to reflux with a slow nitrogen sweep through the flask. Water and amine were condensed and returned. Ammonia was continuously stripped from the reaction mixture.

Evaporation of the flask contents under vacuum at room temperature yielded an off-white solid which was shown by its infrared spectrum to be the TEDA salt of benzoic acid.

EXAMPLE 4

Preparation of diethylamine-adipic acid salt

Adiponitrile (10.8g, 0.1 mole), diethylamine (29.2g, 0.4 mole), and water (51 ml) were heated in the stainless steel cylinder described above for 16 hours at 275°F and 4 hours at 300°F. After cooling and venting, the now homogeneous solution was refluxed as described in example 1. Stripping was stopped when 0.3 moles of ammonia and amine had been liberated from the reaction mixture.

Infrared analysis (AgCl cell) of the solution showed it to be a solution of the desired amine salt.

We claim:
1. A process for hydrolizing at least one member selected from the group consisting of the nitriles, amides and imides of benzoic acid, phthalic acid, isophthalic acid, terephthalic acid, trimellitic acid, trimesic acid, hemimellitic acid, pyromellitic acid, prehnitic acid, mellitic acid, naphthalic acid, 1,8-naphthalene-dicarboxylic acid, 2,6-naphthalene-dicarboxylic acid, 2-, 3- and 4-biphenyl carboxylic acids, diphenic acid, 1-, 2- and 9-anthroic acids, tetrachlorophthalic acid, terephthalamic acid, 4-hydroxyisophthalic acid, phthalaldehydic acid, o-, m- and p-toluic acids, nicotinic acid, isonicotinic acid, picolinic acid, furoic acid, acetic acid, proprionic acid, butyric acid, isobutyric acid, valeric acid, caproic acid, malonic acid, succinic acid, propylmalonic acid, adipic acid, glutaric acid, 2-methylglutaric acid, mucic acid, tartaric acid, citric acid, acrylic, methacrylic acid, ethylacrylic acid, $\beta,\beta$-dimethylacrylic acid, crotonic acid, maleic acid, fumaric acid, allymalonic acid and sorbic acid, comprising:

effecting said hydrolysis with an aqueous amine solution at a temperature of from 100°F to about 500°F; said amine being selected from the group consisting of alkyl amines, hexamethylenetetramine, pyridine, picolines, lutidines, benzyl amine and xylylamine; and removing evolved ammonia to produce the amine salt of the acid.

2. The process of claim 1 wherein the amine is an alkyl amine.
3. The process of claim 2 wherein the amine is a tertiary amine.
4. The process of claim 3 wherein the amine is trimethyl amine.
5. The process of claim 3 wherein the amine is triethyl amine.
6. The process of claim 2 wherein said member is a nitrile.
7. The process of claim 6 wherein said nitrile is an aromatic nitrile.
8. The process of claim 7 wherein said aromatic nitrile contains two cyano groups substituted on adjacent carbon atoms.
9. The process of claim 8 wherein the amine is a tertiary amine.
10. The process of claim 1 wherein said nitrile is terephthalonitrile.
11. The process of claim 10 wherein said amine is an alkyl amine.
12. The process of claim 11 wherein said amine is trimethyl amine.
13. The process of claim 11 wherein said amine is triethyl amine.
14. The process of claim 1 wherein said member is a mixture of phthalonitrile and phthalimide and the amine is a tertiary amine.
15. The process of claim 14 wherein said amine is an alkyl amine.
16. The process of claim 15 wherein said amine is trimethyl amine.
17. The process of claim 15 wherein said amine is triethyl amine.

* * * * *